(12) United States Patent
Modarresi

(10) Patent No.: US 11,117,851 B2
(45) Date of Patent: Sep. 14, 2021

(54) REACTOR LAYOUT FOR METHANOL PRODUCTION FROM LOW QUALITY SYNTHESIS GAS

(71) Applicant: Haldor Topsøe A/S, Kgs. Lyngby (DK)

(72) Inventor: Hassan Modarresi, Lyngby (DK)

(73) Assignee: Haldor Topsoe A/S, Lyngby (DK)

( * ) Notice: Subject to any disclaimer, the term of this patent is extended or adjusted under 35 U.S.C. 154(b) by 0 days.

(21) Appl. No.: 16/727,319

(22) Filed: Dec. 26, 2019

(65) Prior Publication Data

US 2020/0131105 A1    Apr. 30, 2020

Related U.S. Application Data

(62) Division of application No. 15/749,607, filed as application No. PCT/EP2016/066877 on Jul. 15, 2016, now Pat. No. 10,550,055.

(30) Foreign Application Priority Data

Aug. 12, 2015    (DK) .............. PA 2015 00464

(51) Int. Cl.
  *C07C 29/00*       (2006.01)
  *C07C 29/15*       (2006.01)
  (Continued)

(52) U.S. Cl.
  CPC ........... *C07C 29/1518* (2013.01); *B01J 8/001* (2013.01); *B01J 8/0453* (2013.01); *B01J 8/0457* (2013.01);
  (Continued)

(58) Field of Classification Search
  CPC ....... B01J 8/001; B01J 8/02; B01J 8/04; B01J 8/0446; B01J 8/0449; B01J 8/0453; B01J 8/0457; B01J 8/0492; B01J 8/0496; B01J 19/00; B01J 19/0006; B01J 19/0013; B01J 19/0053; B01J 2208/00; B01J 2208/00008; B01J 2208/00017; B01J 2208/00061; B01J 2208/00106; B01J 2208/00168; B01J 2208/00176; B01J 2208/00265; B01J 2208/00274; B01J 2208/0053; B01J 2208/00716; B01J 2219/00; B01J 2219/00049; B01J 2219/00051;
  (Continued)

(56) References Cited

U.S. PATENT DOCUMENTS 4,407,973 A    10/1983  van Dijk et al.
5,252,609 A    10/1993  Pinto
(Continued)

FOREIGN PATENT DOCUMENTS

EP    0 483 919 A2    5/1992
RU    2 289 566 C1    12/2006
(Continued)

*Primary Examiner* — Natasha E Young
(74) *Attorney, Agent, or Firm* — Blank Rome LLP

(57) ABSTRACT

A reactor layout for a process of methanol production from low quality synthesis gas, in which relatively smaller adiabatic reactors can be operated more efficiently, some of the inherent disadvantages of adiabatic reactors for methanol production are avoided. This is done by controlling the outlet temperature in the pre-converter by rapid adjustment of the recycle gas, i.e. by manipulating the gas hourly space velocity in the pre-converter.

3 Claims, 2 Drawing Sheets

(51) Int. Cl.
*C07C 29/151* (2006.01)
*B01J 8/00* (2006.01)
*B01J 8/02* (2006.01)
*B01J 8/04* (2006.01)
*B01J 19/00* (2006.01)
*C07C 31/04* (2006.01)

(52) U.S. Cl.
CPC ........... *B01J 8/0492* (2013.01); *B01J 8/0496* (2013.01); *B01J 19/0013* (2013.01); *B01J 19/0053* (2013.01); *C07C 29/15* (2013.01); *C07C 31/04* (2013.01); *B01J 2208/0053* (2013.01); *B01J 2208/00061* (2013.01); *B01J 2208/00176* (2013.01); *B01J 2208/00274* (2013.01); *B01J 2208/00716* (2013.01); *B01J 2219/00105* (2013.01); *B01J 2219/00202* (2013.01); *B01J 2219/00213* (2013.01); *B01J 2219/00231* (2013.01); *B01J 2219/00389* (2013.01); *C07C 2521/04* (2013.01); *C07C 2523/80* (2013.01)

(58) Field of Classification Search
CPC .... B01J 2219/00074; B01J 2219/00105; B01J 2219/00191; B01J 2219/00193; B01J 2219/00195; B01J 2219/00202; B01J 2219/00211; B01J 2219/00213; B01J 2219/00222; B01J 2219/00227; B01J 2219/00229; B01J 2219/00231; B01J 2219/00274; B01J 2219/00277; B01J 2219/00351; B01J 2219/00389; C07C 29/00; C07C 29/15; C07C 29/151; C07C 29/1512; C07C 29/1516; C07C 29/1518; C07C 31/00; C07C 31/02; C07C 31/04; C07C 2521/00; C07C 2521/02; C07C 2521/04; C07C 2523/00; C07C 2523/70; C07C 2523/76; C07C 2523/80

See application file for complete search history.

(56) References Cited

U.S. PATENT DOCUMENTS

| | | |
|---|---|---|
| 5,827,901 A | 10/1998 | Konig |
| 6,005,011 A | 12/1999 | Henningsen |
| 7,214,721 B2 | 5/2007 | Eastland |
| 2002/0198267 A1 | 12/2002 | Eastland |
| 2005/0020700 A1 | 1/2005 | Bahnisch |
| 2007/0027221 A1 | 2/2007 | Lattner |
| 2007/0225385 A1 | 9/2007 | Early |
| 2012/0322651 A1 | 12/2012 | Schlichting |
| 2014/0031438 A1 | 1/2014 | Heckel et al. |
| 2015/0315109 A1* | 11/2015 | Modarresi ............... C07C 29/32 568/902.2 |

FOREIGN PATENT DOCUMENTS

| | | |
|---|---|---|
| WO | WO-99/59945 | 11/1999 |
| WO | WO 2012/063034 A2 | 5/2012 |
| WO | WO 2014-012601 A1 | 1/2014 |
| WO | WO-2005/115607 A1 | 12/2015 |
| WO | WO-2015/193440 A1 | 12/2015 |

* cited by examiner

REACTOR LAYOUT FOR METHANOL PRODUCTION FROM LOW QUALITY SYNTHESIS GAS

This is a divisional of application Ser. No. 15/749,607, filed on Feb. 1, 2018, now U.S. Pat. No. 10,550,055, which is a 371 of PCT/EP2016/066877, filed on Jul. 15, 2016, published as WO 2017/025272, which claims priority to Denmark Patent Application No. PA 2015 00464, filed on Aug. 12, 2015, the entire disclosures of which are incorporated herein by reference in their entireties.

BACKGROUND OF THE INVENTION

1. Field of the Invention

The present invention relates to a reactor layout for the production of methanol from synthesis gases of low quality.

2. Description of the Related Art

Methanol is synthesized from synthesis gas (syngas), which consists of $H_2$, CO and $CO_2$. The conversion from syngas is performed over a catalyst, which is most often a copper-zinc oxide catalyst on an alumina support. The methanol synthesis catalyst is gradually deactivated over a period of time between one year and five years. The deactivation may be caused by thermal sintering, hydro-thermal sintering and/or poisoning. The most common methanol catalyst poisons are sulfur compounds, such as hydrogen sulfide ($H_2S$), carbon disulfide ($CS_2$), carbonyl sulfide (COS) and organo-sulfur compounds like thiophene ($C_4H_4S$) and methyl thiocyanate ($CH_3SCN$). Furthermore, iron carbonyl ($Fe(CO)_5$) is a poison to avoid, and chlorine (elemental as well as compounds) is a virulent catalyst poison.

Without catalyst poisoning, a longer catalyst lifetime (usually prolonged more than three years) can be expected.

The present invention relates to a novel process for the production of methanol from syngas of low quality, i.e. a syngas with traces of impurities. More specifically the invention relates to a novel reactor layout and operation mode for methanol synthesis from syngas, in which relatively smaller adiabatic reactors can be operated more efficiently, overcoming some of the inherent disadvantages of adiabatic reactors for methanol production. In addition, the adiabatic beds can alternatively play the role of a methanol synthesis catalyst guard, which is installed in the main converter in the synthesis loop. Two or more than two adiabatic reactors guard the methanol synthesis catalyst in the synthesis loop. The catalyst in the adiabatic reactors has a high uptake capacity for poisonous compounds such as chlorine, iron and sulfur. Moreover, the catalyst may be active for methanol synthesis, synthesising the inlet syngas to methanol. In this case, the reactors are also considered as pre-converters.

The main disadvantage of adiabatic reactors for methanol production is the difficulty of obtaining sufficient temperature control across the catalyst bed. Syngas conversion to methanol is extremely exothermic and causes a sharp temperature rise in the catalyst bed unless appropriate means of heat removal are applied. If the reaction heat is not removed from the reactor, the temperature will rise to the equilibrium temperature, which is usually as high as 320° C. or even higher in a typical methanol synthesis converter. Such high temperature will not only generate a considerable amount of by-products; it will also deactivate the catalyst due to thermal sintering phenomena. Thus, temperature control is an important issue in the process of the invention.

The methanol synthesis by conversion from syngas can be formulated as a hydrogenation of either carbon monoxide or carbon dioxide, accompanied by the reverse shift reaction, and can be summarized by the following reaction sequence:

$$CO+2H_2 <-> CH_3OH$$

$$CO_2+3H_2 <-> CH_3OH+H_2O$$

$$CO_2+H_2 <-> CO+H_2O$$

The conversion is performed over a catalyst which, as already mentioned, is most often a copper-zinc oxide catalyst on an alumina support. Examples of this catalyst include applicant's catalysts MK-121 and MK-151 FENCE™.

In methanol plants for production of olefins, the impurity level in the final product is not crucial. Therefore, the operating temperature of the methanol synthesis converter can be as high as possible. In addition, in coal-based methanol plants there are always some poisonous compounds present, such as chlorine and sulfurous compounds, which can gradually deactivate the methanol synthesis catalyst and thus shorten the catalyst life. To remove these harmful compounds, purification and guard reactors are proposed and practiced. Thus, U.S. Pat. No. 6,005,011 describes a plant and a process for converting associated gas from crude oil to methanol, said plant comprising a sulfur guard in the shape of a desulfurization unit containing a ZnO bed. In U.S. Pat. No. 4,407,973, a process for producing methanol through steam reforming of natural gas and partial oxidation of coal is disclosed. This process also includes a sulfur guard in the form of a guard chamber, in which traces of sulfur are removed from the compressed gas.

US 2007/0225385 discloses a process for the production of methanol, said process comprises the use of a first and a second reactor. Addition of make-up gas to the first reactor allows the partial pressure in each reactor to be adjusted, thus providing a level of control over the amount of reaction taking place in each reactor. This in turn allows control of the peak temperatures in each reactor, and an acceptable catalyst life time is achieved. An adiabatic pre-converter may be included upstream of the first reactor to allow lower feed temperatures. There is no disclosure regarding the type of reactor used as the first reactor. Furthermore, partial pressures, control of flow rate and split of make-up gas between the reactors contribute to temperature control and thus to catalyst bed temperatures. However, there is no disclosure of temperature control as in the present invention.

In US 2002/0198267, a process similar to the process of the present invention is disclosed, where a first adiabatic reactor containing a first volume of catalyst is combined with a downstream cooled second reactor containing a second volume of catalyst, which is designed to meet the additional requirement to control the reaction temperature. Furthermore, the maximum temperature achieved in the reaction zones is reduced, which in turn will reduce the rate at which catalyst deactivation occurs. It is stated that temperature sensors, control valves and the like may be required in a commercial plant and may fall under conventional chemical engineering practice. But again, there is no disclosure of temperature control as in the present invention.

WO 2015/193440 belonging to the Applicant describes a system for production of methanol comprising two reactors in series connection, each of which being connected to a feed-effluent heat exchanger, a cooler and a separator. A purge can be taken out, preferably from the final recycle stream.

A system similar to that of WO 2015/193440, but being without feed-effluent heat exchangers and using a copper catalyst, is disclosed in WO 2005/115607. The present invention differs from the subject-matter of WO 2005/115607 in that the temperature of the effluent from the pre-converter is controlled by adjusting the amount of recycled synthesis gas which is added to the inlet of the pre-converter. A further difference is that, in the present invention, care is taken to avoid catalyst overheating.

Applicant's published WO 2014/012601 A1 discloses a process and a reaction system for the preparation of methanol comprising two parallel reaction units, wherein the first unit is operated on a mixture of fresh synthesis gas and unconverted synthesis gas, while the second unit is operated with unconverted synthesis gas only. Regarding the reactor types which can be used, the WO publication discloses that the first and second methanol reaction unit can comprise one or more reactors selected from boiling water cooled reactors, gas cooled reactors, quench reactors and adiabatically operated reactors, connected in series and/or in parallel.

While two reactors in parallel are used in Applicant's above WO publication, the process of the present invention is operated with two reactors in series, i.e. one adiabatic pre-converter on stream in series with one quench converter. In fact, the process of the invention uses two pre-converters (dual) in parallel, of which only one is on stream, whereas the two parallel reaction units described in the WO publication are simultaneously on stream. Moreover, in the process of the invention all the effluent from the pre-converter is transferred to the second reaction unit, whereas in the process of the WO publication the effluent from the first reaction unit is not directly transferred to the second reaction unit.

The basic idea underlying the present invention is to control the outlet adiabatic temperature in the pre-converter by a rapid adjustment of the recycle gas flow if this is necessary, i.e. by manipulation of the GHSV (gas hourly space velocity) in the pre-converter. This means that the adiabatic reactors are not intended to operate on mixed make-up and recycle gas, but solely on make-up gas. A fraction of recycle gas flow is added to the inlet of the adiabatic reactor, if it is necessary to increase the GHSV of the reactor in order to control the temperature in the outlet from the adiabatic reactor. In other words, the adiabatic reactors are designed to operate on make-up gas flow. The recycle gas addition is practiced if, for example, part load operation is desired. The control system injects recycle gas to the make-up gas automatically in order to keep the adiabatic outlet temperature below a critical limit for methanol synthesis catalyst.

The invention allows the plant operators to reliably operate the adiabatic bed converters, even at part load. This idea is not disclosed in the WO publication or in any other prior art documents. Another feature is to use a dual pre-converter or multiple pre-converters to protect the main converter from poisons and undesirable peak temperatures.

The idea discloses a new process layout with a novel operational philosophy to overcome some fundamental disadvantages of packed bed reactors in methanol synthesis. It is also intended to be able to operate a methanol plant for a longer time than a typical methanol plant which must be shut down due to catalyst deactivation and poisoning. The pre-converted syngas, i.e. the effluent from the pre-converter, is less aggressive towards the methanol synthesis since the carbon monoxide to carbon dioxide ratio is reduced in the pre-converter. The temperature peak in the main converter then would be lower than in the case where fresh unconverted make-up gas is introduced. This would, in addition, protect the catalyst in the main converter against accelerated thermal sintering, which is exacerbated at high temperatures.

It has been of great interest in the recent years to size and build high capacity methanol plants for economic reasons. However, scaling up certain complex methanol converters to large size is a great challenge, both in terms of technical complexity and capital investment. It is desirable to use cheap and simple converters in large methanol plants. An adiabatic converter is the most simple and also the cheapest converter which may be used. However, due to technical and process challenges, its suitability for the purpose is questionable.

As already mentioned, the main disadvantage of adiabatic reactors for methanol production is the difficulty of obtaining sufficient temperature control across the catalyst bed. Therefore, the present invention is concerned with a process design and a method for methanol production from synthesis gas, wherein adiabatic reactors can be operated efficiently and effectively, thereby overcoming some of the inherent disadvantages of adiabatic reactors for methanol production. The process design and the method for methanol production according to the invention are especially suitable for large methanol plants based on coal gasification.

SUMMARY OF THE INVENTION

Thus, the present invention relates to a reactor layout and process for methanol production from synthesis gas comprising the following steps:
  providing a fresh, pressurized methanol synthesis gas containing hydrogen, carbon monoxide and carbon dioxide, which is pre-heated and passed through a methanol pre-converter, in which the synthesis gas is partially converted to methanol over a heterogeneous methanol catalyst,
  providing a recycle gas stream containing partly converted methanol synthesis gas and mixing a part of the recycle stream with the fresh synthesis gas (make-up gas) to a process gas stream,
  cooling the process gas stream from the pre-converter/guard reactor to a temperature, which is suitable for the main converter, and passing the cooled process gas stream to a conventional methanol synthesis loop, preferably with a boiling water reactor (BWR), and
  separating raw methanol from the synthesis loop,
wherein the outlet adiabatic temperature in the pre-converter is controlled by rapid adjustment of the recycle gas if it is necessary, i.e. by manipulation of the GHSV (gas hourly space velocity) in the pre-converter.

In a conventional methanol synthesis loop, one or more reactors connected in series are operated either on fresh synthesis gas diluted with recycled unconverted gas separated from the reactor effluents or on the reactor effluent containing methanol and unconverted synthesis gas. The recycle ratio (recycle gas to fresh synthesis feed gas) is from 1.5:1 up to 7:1 in normal practice.

BRIEF DESCRIPTION OF THE DRAWINGS

The invention is illustrated further with reference to the drawings, in which.

DETAILED DESCRIPTION OF THE PREFERRED EMBODIMENTS

Figure 1:
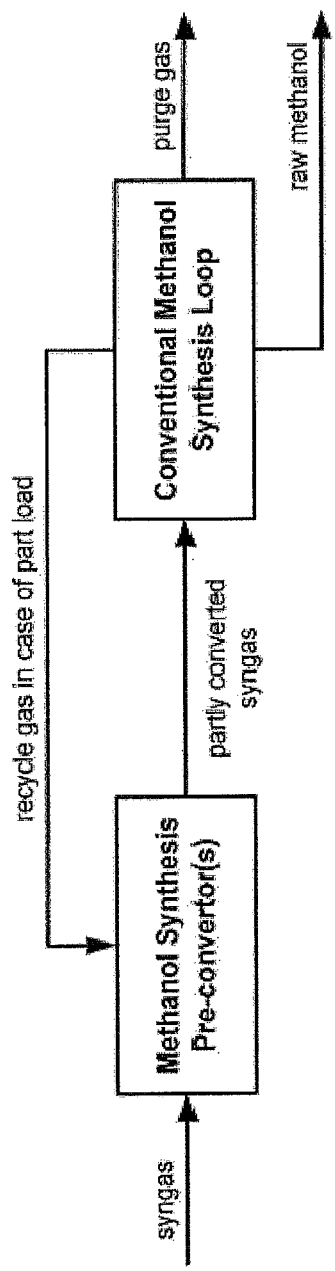
FIG. 1 is a block diagram showing the methanol synthesis process according to the invention.

In the process of the invention for methanol production from synthesis gas, one or more pre-converter(s) for methanol synthesis is/are followed by a conventional methanol synthesis loop. In the present context, a pre-converter is a methanol converter that only receives feed synthesis gas in full load operation. The main methanol converter in the conventional methanol synthesis loop converts a mixture of recycle gas and the effluent gas from the pre-converter. The pre-converter may be fed with a fraction of the recycle gas from the synthesis loop in part load condition, whereas a safe gas space velocity across the reactor is required to avoid overheating of the catalyst in the reactor; see FIG. 1.

In the conventional methanol synthesis loop, the methanol converters are often boiling water reactors (BWR), i.e. tubular reactors with catalyst loaded into several tubes surrounded by water on the shell side. The boiling water efficiently removes the heat liberated by the methanol synthesis reaction and thus ensures an almost isothermal reaction path at conditions close to the maximum rate of reaction. This not only ensures a high conversion per pass and thus a high catalyst utilisation as well as a low recirculation, but also a low by-product formation.

Adiabatic converters are widely used for methanol synthesis, and a synthesis loop with adiabatic reactors as methanol converters normally comprises a number (e.g. 2-4) of fixed bed reactors arranged in series with cooling between the reactors.

Further, the methanol converters can be quench reactors. A quench reactor consists of a number of adiabatic catalyst beds installed in series within one pressure shell. In practice, up to around five catalyst beds can be used. The reactor feed is split into several fractions and then distributed to the synthesis reactor between the individual catalyst beds.

Figure 2:
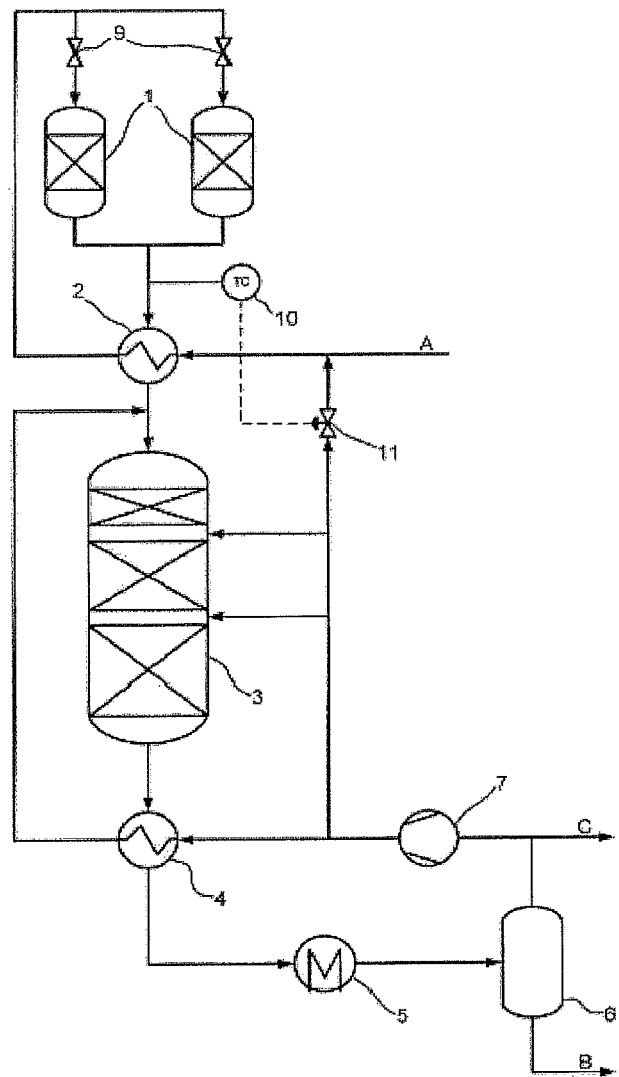
FIG. 2 is a drawing illustrating an example of a process layout.

With reference to FIG. 2, the following is an example of a process layout according to the invention:

Pressurized synthesis gas A is pre-heated in a feed-effluent heat exchanger 2 and passed through one of the methanol pre-converters/guard reactors 1, in which synthesis gas is partially converted to methanol over a heterogeneous methanol synthesis catalyst. Traces of impurities are also removed in the reactor. The extent of conversion is dictated by the pre-converter outlet temperature. In part load condition, in which the gas space velocity drops from the design point (designed for full load condition), the outlet temperature will rise. A maximum allowable outlet temperature is defined and controlled 10 using a cold recycle gas stream which is injected to the pre-converter inlet via the control valve 11. An alternative control approach would be to fix the gas space velocity in the pre-converter in part load, i.e. to compensate the synthesis gas flow drop by the recycle gas. The latter approach may be practiced if the poisonous content of the make-up gas is negligible, meaning that the deactivation due to poisoning is not a dominant mechanism. Nevertheless, relying on the adiabatic reactor outlet temperature is a reliable strategy to protect the guard bed and control the product quality (low by-product formation).

Two or more pre-converters/guard reactors are installed in parallel whereas only one pre-converter is on stream. The other pre-converter(s)/guard reactor(s) is/are isolated by the inlet valve 9. The effluent from the pre-converter/guard reactor is cooled to a temperature, which is suitable for the main converter, in the feed-effluent heat exchanger 2, and subsequently it enters a conventional methanol synthesis loop. In this example, the conventional methanol synthesis loop is presented by a main methanol converter 3, a main feed-effluent heat exchanger 4, a cooler or a series of coolers 5, a high pressure gas-liquid separator 6, which splits the inlet flow into raw methanol B and recycle gas, and a recycle compressor 7. The loop purge C is drawn from the recycle gas before the recycle compressor.

The process layout described above is only one example of a useful layout, and a number of variations are possible, such as:

- any other type of main methanol converter,
- any type of pre-converter/guard reactor,
- MUG (make-up gas) splitting on the cold side, i.e. before the feed-effluent heat exchanger 4,
- the number of pre-converters/guard reactors,
- on-stream catalyst replacement in pre-converters/guard reactors,
- use of low-activity catalysts in the pre-converters/guard reactors and a high-activity catalyst in the main converter, and
- catalyst replacement in the pre-converters/guard reactors during operation.

What is claimed is:

1. A reactor layout for carrying out a process for methanol production from synthesis gas, said reactor layout comprising:
    one or more methanol pre-converters/guard reactors, in which the synthesis gas is partially converted to methanol over a heterogeneous catalyst to generate an effluent gas without impurities,
    a feed-effluent heat exchanger for pre-heating the synthesis gas and for cooling the effluent gas from the one or more methanol pre-converters/guard reactors, and
    a methanol synthesis loop comprising:
    a main methanol converter for converting a mixture of recycle gas and the cooled effluent gas from the one or more methanol pre-converters/guard reactors,
    a main feed-effluent heat exchanger,
    a cooler or a series of coolers,
    a high pressure gas-liquid separator, which splits the inlet flow into raw methanol and recycle gas,
    a recycle compressor,
    a loop purge, wherein the loop purge is drawn from the recycle gas before the recycle compressor, and
    means for defining and controlling a maximum allowable outlet temperature using a cold recycle gas stream which is injected into the one or more methanol pre-converters/guard reactors via a control valve.

2. The reactor layout according to claim 1, which has fresh feed gas splitting located on the cold side, before the feed-effluent heat exchanger.

3. The reactor layout according to claim 1, which enables on-stream catalyst replacement in the one or more pre-converters/guard reactors.

* * * * *